United States Patent
Wang et al.

(10) Patent No.: US 9,527,783 B2
(45) Date of Patent: Dec. 27, 2016

(54) CATALYST FOR METHANATION OF CARBON DIOXIDE, PREPARATION METHOD AND USAGE THEREOF

(71) Applicant: Wuhan Kaidi Engineering Technology Research Institute Co., Ltd., Wuhan (CN)

(72) Inventors: Zhilong Wang, Wuhan (CN); Yanfeng Zhang, Wuhan (CN); Yilong Chen, Wuhan (CN); Yongjie Xue, Wuhan (CN); Leiming Tao, Wuhan (CN); Zhixiang Luo, Wuhan (CN); Xingcai Zheng, Wuhan (CN)

(73) Assignee: WUHAN KAIDI ENGINEERING TECHNOLOGY RESEARCH INSTITUTE CO., LTD., Wuhan (CN)

( * ) Notice: Subject to any disclaimer, the term of this patent is extended or adjusted under 35 U.S.C. 154(b) by 0 days.

(21) Appl. No.: 15/199,937

(22) Filed: Jun. 30, 2016

(65) Prior Publication Data
US 2016/0311729 A1    Oct. 27, 2016

Related U.S. Application Data

(60) Division of application No. 14/242,816, filed on Apr. 1, 2014, now Pat. No. 9,388,091, which is a continuation-in-part of application No. PCT/CN2012/083095, filed on Oct. 17, 2012.

(30) Foreign Application Priority Data

Oct. 19, 2011   (CN) .......................... 2011 1 0317947

(51) Int. Cl.
*B01J 21/08*   (2006.01)
*C07C 27/00*   (2006.01)
*C07C 1/12*    (2006.01)
*B01J 21/18*   (2006.01)
*B01J 23/755*  (2006.01)
*B01J 37/08*   (2006.01)
*B01J 37/04*   (2006.01)

(52) U.S. Cl.
CPC ................ *C07C 1/12* (2013.01); *B01J 21/18* (2013.01); *B01J 23/755* (2013.01); *B01J 37/04* (2013.01); *B01J 37/08* (2013.01); *C07C 2521/18* (2013.01); *C07C 2523/755* (2013.01)

(58) Field of Classification Search
CPC ......... B01J 37/084; B01J 37/082; B01J 37/08; B01J 21/18; B01J 23/755; C07C 1/12; C10G 2/32
USPC ................................ 502/185; 518/700, 715
See application file for complete search history.

(56) References Cited

PUBLICATIONS

Chang et al., nickel supported on rice husk ash, (Applied Catalysis A: General 164 (1997) 225-236).*
Liao et al., Distribution and enrichment of trace elements in ashes from biomass gasification power plant ( Ranliao Huaxue Xuebao (2005), 33(4), Abstract only).*

* cited by examiner

*Primary Examiner* — Jafar Parsa
(74) *Attorney, Agent, or Firm* — Matthias Scholl P.C.; Matthias Scholl

(57) ABSTRACT

A catalyst for methanation of carbon dioxide, a method of preparing the catalyst, and a method of hydrogenating carbon dioxide in the presence of the catalyst in a fixed bed reactor are disclosed. The catalyst is formed by mixing ash from a biomass power plant with a nickel compound and calcining the resulting mixture. The catalyst formed by calcination includes between 2 and 20 wt. % of nickel supported on ash from combusting biomass.

7 Claims, No Drawings

CATALYST FOR METHANATION OF CARBON DIOXIDE, PREPARATION METHOD AND USAGE THEREOF

CROSS-REFERENCE TO RELATED APPLICATIONS

This application is a divisional of and claims domestic priority benefits to U.S. Ser. No. 14/242,816 filed on Apr. 1, 2014, now pending, which is a continuation-in-part of International Patent Application No. PCT/CN2012/083095 with an international filing date of Oct. 17, 2012, designating the United States, which is now abandoned as to the United States and further claims priority benefits to Chinese Patent Application No. 201110317947.1 filed Oct. 19, 2011. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, and Cambridge, Mass. 02142.

BACKGROUND OF THE INVENTION

Field of the Invention

The invention relates to the catalytic synthesis technology, and more particularly to a catalyst for methanation of carbon dioxide, a preparation method and application thereof.

Description of the Related Art

Conventional catalysts for methanation of carbon dioxide include alumina as the carrier and a single nickel or a nickel mixed with a single rear earth element as an active ingredient. Such catalysts have a relatively low catalytic activity and require harsh reaction conditions, including relatively high pressure, low speed, and overdose of hydrogen, thereby resulting in high investment and low output.

In another respect, the biomass power plant mainly generates electric power through the direct combustion of the agricultural and forestry waste. With the continuous development of the biomass power industry, tough issues were brought in, such as the difficulty in the combustion of the solid waste in the biomass power plant, and particularly the difficulty in the resource utilization of ash (plant ash and rice husk ash) of the biomass power plant. In the ash from the biomass power plant, a primary composition is $SiO_2$ and auxiliary compositions include $Al_2O_3$, $CaO$, $Fe_2O_3$, $TiO_2$, $MgO$, and $K_2O$, among which a plurality of metal oxides have activation ability. Most of the ash from the biomass power plant has not been effectively utilized so far.

SUMMARY OF THE INVENTION

In view of the above-described problems, it is one objective of the invention to provide a catalyst for methanation of carbon dioxide, a method for preparing the same, and a method for using the same. The catalyst is prepared by using wasted ash from combustion of biomass as a carrier and using nickel as an active ingredient.

To achieve the above objective, there is provided a catalyst for methanation of carbon dioxide. The catalyst is formed by mixing ash from a biomass power plant with a nickel compound and calcining a resulting mixture. The catalyst formed by calcination comprises between 2 and 20 wt. % of nickel.

In a class of this embodiment, the nickel compound is selected from the group consisting of nickel nitrate, nickel oxalate, nickel formate, nickel acetate, nickel citrate, nickel tartrate, and a mixture thereof. The easily decomposable nickel compounds are capable of providing sufficient active ingredients for the carrier of the ash from the biomass power plant.

In a class of this embodiment, the catalyst formed in the calcination comprises between 5 and 15 wt. % of nickel.

In a class of this embodiment, the catalyst formed in the calcination comprises between 10 and 20 wt. % of nickel.

In a class of this embodiment, the ash from the biomass power plant is collected in a bag dust collector. An average particle size of the ash from the biomass power plant is between 10 and 15 μm, so that the active ingredients of nickel and the carrier of the ash from the biomass power plant are well fused in the calcination process.

A method for preparing the catalyst for methanation of carbon dioxide, the method comprises the following steps:

1) preparing an aqueous solution comprising between 5 and 30 wt. % of the nickel compound;

2) calcining the ash from the biomass power plant at a temperature of between 300 and 400° C. for between 20 and 40 min for removing combustible impurities from the ash from the biomass power plant;

3) calculating doses of raw materials according to a desired weight percent of nickel in a catalyst product, mixing the aqueous solution comprising the nickel compound with the ash from the biomass power plant after calcinations in step 2), and stirring a resulting mixture for between 5 and 10 h for uniformly impregnating the mixture;

4) desiccating the ash from the biomass power plant after impregnation treatment at a temperature of between 110 and 150° C. for between 0.5 and 1.5 h; and 5) calcining the ash from the biomass power plant after desiccation treatment at a temperature of between 400 and 500° C. for between 3 and 6 h to yield the catalyst for methanation of carbon dioxide.

Preferably, a calcination time in step 2) is controlled for between 25 and 30 min; a stirring time in step 3) is controlled for between 6 and 8 h; a desiccation time in step 4) is controlled for between 0.5 and 1.0 h; and a calcinations time in step 5) is controlled for between 4 and 5 h.

A method for hydrogenation of carbon dioxide in a fixed bed reactor comprising applying the catalyst. Specifically, activation conditions of the catalyst are as follows: a particle size of the catalyst is between 40 and 60 meshes; a reaction pressure is normal pressure; a molar ratio between feed compositions is $H_2/CO_2=4/1$; a volume space velocity is between 5500 and 9000 $h^{-1}$; a reaction temperature is between 250 and 450° C.; and a reaction time is between 1 and 2 h.

Preferably, the activation conditions of the catalyst are as follows: the particle size of the catalyst is between 40 and 60 meshes; the reaction pressure is normal pressure; the molar ratio between feed compositions is $H_2/CO_2=4/1$; the volume space velocity is between 6000 and 8000 $h^{-1}$; the reaction temperature is between 350 and 400° C.; and the reaction time is 2 h.

Advantages of the invention are as follows: first, the catalyst carrier of the invention is directly selected from the ash from the biomass power plant, not only does it has a wide source and low cost, but also it changes waste into valuable and reaches the recycling of the waste, thereby solving the problem that the waste from the combustion in the biomass power plant is difficult to be treated. Second, the ash from the biomass power plant that is naturally mixed with a plurality of metals or metal oxides comprising a primary composition of $SiO_2$ and auxiliary compositions comprising $Al_2O_3$, CaO, $Fe_2O_3$, $TiO_2$, MgO, and $K_2O$, so that as the catalyst carrier, the ash from the biomass power plant is not required to add with other additives. The content of the active ingredient of nickel in the carrier is controlled within 20 wt. %, and preferably between 10 and 20 wt. %, thereby largely decreasing the production cost. Third, the average particle size of the ash from the biomass power plant is controlled at between 10 and 15 μm, the specific area is large, and the nickel or the compound thereof is loaded without mechanical crushing process, thereby further saving the production cost. Fourth, multi-metal oxide in the ash from the biomass power plant is capable of carrying nickel, enhancing the activity of the nickel on the $SiO_2$ carrier, as well as regulating performances of the surface area, pore volume, and average pore radius of the carrier. Besides, the multi-metal oxide in the ash from the biomass power plant can be easily reduced and has excellent activity at low temperature and low production cost.

In summary, the catalyst of the invention not only has relatively high catalytic activity and selectivity but also has a much higher stability; the catalyst is capable of effectively catalyzing the hydrogenation of carbon dioxide in the normal pressure and facilitates the transformation of the carbon dioxide into the methane. The preparation method of the invention is capable of changing waste into valuable, and the operation thereof is simple. The cost of the preparation method from the source of the raw material to the manufacture of the production is very low, thereby being particularly suitable to the resource utilization of the ash from the biomass power plant.

DETAILED DESCRIPTION OF THE EMBODIMENTS

For further illustrating the invention, experiments detailing a catalyst for methanation of carbon dioxide, a preparation method and a usage thereof are described hereinbelow, but the content of the invention is not limited by the following examples.

Example 1

A method for preparing a catalyst comprising 5 wt. % of nickel for methanation of carbon dioxide (a content of nickel accounts for approximately 5 wt. % of a total weight of the catalyst, and remainders comprise ash from a biomass power plant and inevitable impurities).

1) 1.441 g of nickel nitrate hexahydrate was added to a Bunsen beaker, deionized water was added to dissolve the nickel nitrate hexahydrate, a resulting solution was transferred to a 45 mL volumetric flask and calibrated to yield a nickel nitrate solution;

2) ash from a biomass power plant was calcined at the temperature of 300° C. for 40 min, and combustible impurities comprising $H_2O$, C, and $SO_3$ were removed from the ash;

3) 10 g of the ash from the biomass power plant after calcinations was added to an evaporating dish, 45 mL of the nickel nitrate solution was transferred from the volumetric flask to the evaporating dish for impregnating the mixture of biomass power plant, and a resulting mixture was stirred for 5 h;

4) the ash from the biomass power plant after the impregnation treatment was desiccated at the temperature of 120° C. for 1.0 h; and 5) the ash from the biomass power plant after the desiccation was placed in a muffle furnace and then calcined at the temperature of 450° C. for 5 h for decomposing salt therein, thereafter, the temperature was decreased to the room temperature, and the catalyst comprising 5 wt. % of nickel for methanation of carbon dioxide was yielded.

Application and analysis detection of the catalyst comprising 5 wt. % of nickel for methanation of carbon dioxide were as follows:

The catalyst comprising 5 wt. % of nickel for methanation of carbon dioxide was screened to obtain particles having a particle size of between 40 and 60 meshes. 1 g of the catalyst comprising 5 wt. % of nickel for methanation of carbon dioxide obtained from the screening treatment was placed in a fixed bed reactor. The fixed bed reactor was then heated to the temperature of 400° C. and $H_2$ having a flow of 100 mL/min was introduced for 1 h for reduction. After that, mixed reaction gases having a molar ratio of $H_2/CO_2=4/1$ were introduced, and a product was analyzed and detected on line by gas chromatography under the following conditions: a reaction temperature of between 250 and 450° C., a reaction pressure of 0.1 MPa, a vacuum space velocity of between 5500 and 9000 $h^{-1}$, and a circulating reaction time of 2 h. When the reaction temperature was 400° C., and the vacuum space velocity was 6000 $h^{-1}$, a conversion rate of $CO_2$ was 91.36 wt. %.

Example 2

A method for preparing a catalyst comprising 10 wt. % of nickel for methanation of carbon dioxide (a content of nickel accounts for 10 wt. % of a total weight of the catalyst, and remainders comprise ash from a biomass power plant and inevitable impurities).

1) 3.367 g of nickel nitrate hexahydrate was added to a Bunsen beaker, deionized water was added to dissolve the nickel nitrate hexahydrate, a resulting solution was transferred to a 45 mL volumetric flask and calibrated to yield a nickel nitrate solution;

2) ash from a biomass power plant was calcined at the temperature of 350° C. for 30 min, and combustible impurities comprising $H_2O$, C, and $SO_3$ were removed from the ash;

3) 10 g of the ash from the biomass power plant after calcinations was added to an evaporating dish, 45 mL of the nickel nitrate solution was transferred from the volumetric flask to the evaporating dish for impregnating the mixture of biomass power plant, and a resulting mixture was stirred for 6 h;

4) the ash from the biomass power plant after the impregnation treatment was desiccated at the temperature of 150° C. for 1.5 h; and 5) the ash from the biomass power plant after the desiccation was placed in a muffle furnace and then calcined at the temperature of 450° C. for 6 h for decomposing salt therein, thereafter, the temperature was decreased to the room temperature, and the catalyst comprising 10 wt. % of nickel for methanation of carbon dioxide was yielded.

Application and analysis detection of the catalyst comprising 10 wt. % of nickel for methanation of carbon dioxide were as follows:

The catalyst comprising 10 wt. % of nickel for methanation of carbon dioxide was screened to obtain particles having a particle size of between 40 and 60 meshes. 1 g of the catalyst comprising 10 wt. % of nickel for methanation of carbon dioxide obtained from the screening treatment was placed in a fixed bed reactor. The fixed bed reactor was then heated to the temperature of 400° C. and $H_2$ having a flow of 100 mL/min was introduced for 1 h for reduction. After that, mixed reaction gases having a molar ratio of $H_2/CO_2=4/1$ were introduced, and a product was analyzed and detected on line by gas chromatography under the following conditions: a reaction temperature of between 250 and 450° C., a reaction pressure of 0.1 MPa, a vacuum space velocity of between 5500 and 9000 $h^{-1}$, and a circulating reaction time of 2 h. When the reaction temperature was 300° C., and the vacuum space velocity was 7000 $h^{-1}$, a conversion rate of $CO_2$ was 95.21 wt. %.

Example 3

A method for preparing a catalyst comprising 15 wt. % of nickel for methanation of carbon dioxide (a content of nickel accounts for 15 wt. % of a total weight of the catalyst, and remainders comprise ash from a biomass power plant and inevitable impurities).

1) 6.073 g of nickel nitrate hexahydrate was added to a Bunsen beaker, deionized water was added to dissolve the nickel nitrate hexahydrate, a resulting solution was transferred to a 45 mL volumetric flask and calibrated to yield a nickel nitrate solution;

2) ash from a biomass power plant was calcined at the temperature of 350° C. for 30 min, and combustible impurities comprising $H_2O$, C, and $SO_3$ were removed from the ash;

3) 10 g of the ash from the biomass power plant after calcinations was added to an evaporating dish, 45 mL of the nickel nitrate solution was transferred from the volumetric flask to the evaporating dish for impregnating the mixture of biomass power plant, and a resulting mixture was stirred for 7 h;

4) the ash from the biomass power plant after the impregnation treatment was desiccated at the temperature of 150° C. for 0.5 h; and 5) the ash from the biomass power plant after the desiccation was placed in a muffle furnace and then calcined at the temperature of 450° C. for 4 h for decomposing salt therein, thereafter, the temperature was decreased to the room temperature, and the catalyst comprising 15 wt. % of nickel for methanation of carbon dioxide was yielded.

Application and analysis detection of the catalyst comprising 15 wt. % of nickel for methanation of carbon dioxide were as follows:

The catalyst comprising 15 wt. % of nickel for methanation of carbon dioxide was screened to obtain particles having a particle size of between 40 and 60 meshes. 1 g of the catalyst comprising 15 wt. % of nickel for methanation of carbon dioxide obtained from the screening treatment was placed in a fixed bed reactor. The fixed bed reactor was then heated to the temperature of 400° C. and $H_2$ having a flow of 100 mL/min was introduced for 1 h for reduction. After that, mixed reaction gases having a molar ratio of $H_2/CO_2=4/1$ were introduced, and a product was analyzed and detected on line by gas chromatography under the following conditions: a reaction temperature of between 250 and 450° C., a reaction pressure of 0.1 MPa, a vacuum space velocity of between 5500 and 9000 $h^{-1}$, and a circulating reaction time of 2 h. When the reaction temperature was 400° C., and the vacuum space velocity was 7000 $h^{-1}$, a conversion rate of $CO_2$ was 97.87 wt. %.

Example 4

A method for preparing a catalyst comprising 20 wt. % of nickel for methanation of carbon dioxide (a content of nickel accounts for 20 wt. % of a total weight of the catalyst, and remainders comprise ash from a biomass power plant and inevitable impurities).

1) 10.152 g of nickel nitrate hexahydrate was added to a Bunsen beaker, deionized water was added to dissolve the nickel nitrate hexahydrate, a resulting solution was transferred to a 45 mL volumetric flask and calibrated to yield a nickel nitrate solution;

2) ash from a biomass power plant was calcined at the temperature of 400° C. for 20 min, and combustible impurities comprising $H_2O$, C, and $SO_3$ were removed from the ash;

3) 10 g of the ash from the biomass power plant after calcinations was added to an evaporating dish, 45 mL of the nickel nitrate solution was transferred from the volumetric flask to the evaporating dish for impregnating the mixture of biomass power plant, and a resulting mixture was stirred for 8 h;

4) the ash from the biomass power plant after the impregnation treatment was desiccated at the temperature of 150° C. for 1.0 h; and 5) the ash from the biomass power plant after the desiccation was placed in a muffle furnace and then calcined at the temperature of 450° C. for 3 h for decomposing salt therein, thereafter, the temperature was decreased to the room temperature, and the catalyst comprising 20 wt. % of nickel for methanation of carbon dioxide was yielded.

Application and analysis detection of the catalyst comprising 20 wt. % of nickel for methanation of carbon dioxide were as follows:

The catalyst comprising 20 wt. % of nickel for methanation of carbon dioxide was screened to obtain particles having a particle size of between 40 and 60 meshes. 1 g of the catalyst comprising 20 wt. % of nickel for methanation of carbon dioxide obtained from the screening treatment was placed in a fixed bed reactor. The fixed bed reactor was then heated to the temperature of 400° C. and $H_2$ having a flow of 100 mL/min was introduced for 1 h for reduction. After that, mixed reaction gases having a molar ratio of $H_2/CO_2=4/1$ were introduced, and a product was analyzed and detected on line by gas chromatography under the following conditions: a reaction temperature of between 250 and 450° C., a reaction pressure of 0.1 MPa, a vacuum space velocity of between 5500 and 9000 $h^{-1}$, and a circulating reaction time of 2 h. When the reaction temperature was 400° C., and the vacuum space velocity was 6000 $h^{-1}$, a conversion rate of $CO_2$ was 96.91 wt. %.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing a catalyst for methanation of carbon dioxide, the method comprising:
  1) preparing an aqueous solution comprising between 5 and 30 wt. % of a nickel compound;
  2) calcining ash from the biomass power plant at a temperature of between 300 and 400° C. for between 20 and 40 min for removing combustible impurities from the ash to obtain a second ash, wherein the ash from the biomass power plant and the second ash comprise SiO2, Al2O3, CaO, Fe2O3, TiO2, MgO, and K2O;

3) mixing the aqueous solution obtained in 1) with the second ash obtained in 2), and stirring a resulting mixture for between 5 and 10 h for uniformly impregnating the mixture;

4) desiccating the mixture obtained in 3) at a temperature of between 110 and 150° C. for between 0.5 and 1.5 h; and 5) calcining the mixture obtained in 4) at a temperature of between 400 and 500° C. for between 3 and 6 h to yield the catalyst.

2. The method of claim 1, wherein a calcination time in 2) is controlled for between 25 and 30 min;

a stirring time in 3) is controlled for between 6 and 8 h;

a desiccation time in 4) is controlled for between 0.5 and 1.0 h; and a calcination time in 5) is controlled for between 4 and 5 h.

3. The method of claim 1, wherein the nickel compound is selected from the group consisting of nickel nitrate, nickel oxalate, nickel formate, nickel acetate, nickel citrate, nickel tartrate, and a mixture thereof.

4. The method of claim 1, wherein the ash from the biomass power plant has an average particle size of between 10 and 15 µm.

5. The method of claim 1, wherein the catalyst comprises between 2 and 20 wt. % of nickel.

6. A method for hydrogenation of carbon dioxide in a fixed bed reactor, the method comprising reacting carbon dioxide and hydrogen in the fixed bed reactor, and adding a catalyst to the fixed bed reactor, wherein:

the catalyst comprises between 2 and 20 wt. % of nickel supported on ash, and the ash comprises $SiO_2$, $Al_2O_3$, $CaO$, $Fe_2O_3$, $TiO_2$, $MgO$, and $K_2O$;

a particle size of the catalyst is between 40 and 60 meshes;

a reaction pressure is normal pressure;

a molar ratio of $H_2$ to $CO_2$ is 4/1;

a volume space velocity is between 5500 and 9000 $h^{-1}$;

a reaction temperature is between 250 and 450° C.; and a reaction time is between 1 and 2 h.

7. The method of claim 6, wherein:

the volume space velocity is between 6000 and 8000 $h^{-1}$;

the reaction temperature is between 350 and 400° C.; and the reaction time is 2 h.

* * * * *